US00PP26018P3

(12) United States Plant Patent
Olesen

(10) Patent No.: US PP26,018 P3
(45) Date of Patent: Oct. 27, 2015

(54) MINIATURE ROSE PLANT NAMED 'POULPAL055'

(50) Latin Name: ***Rosa* hybrid**
Varietal Denomination: Poulpal055

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 183 days.

(21) Appl. No.: 13/986,934

(22) Filed: Jun. 14, 2013

(65) Prior Publication Data

US 2014/0373217 P1 Dec. 18, 2014

(51) Int. Cl.
*A01H 5/02* (2006.01)

(52) U.S. Cl.
USPC ..... Plt./121

(58) Field of Classification Search
USPC ..... Plt./101, 116, 121
See application file for complete search history.

(56) References Cited

PUBLICATIONS

UPOV-Pluto Plant Variety Database International Union for the Protection of New Varieties of Plants, Jan. 19, 2015, obtained for cultivar name 'Poulpal055' (1 page total).*
Poulsen Roser A/S catalog; Retrieved from the Internet http://www.poulsenroser.com (1 page total).*
'HelpMeFind' website; Retrieved from the Internet http://www.helpmefind.com (1 page total).*

* cited by examiner

*Primary Examiner* — Susan McCormick Ewoldt

(57) ABSTRACT

A new miniature rose plant that has abundant, pink flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpal055'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpal055', originated as a single seedling from the stated cross.

The new variety may be distinguished from its male pollen parent and female seed parent primarily by flower coloration and growth habit. The female seed parent plant has apricot colored flowers, while the claimed plant has pink flowers. The male pollen parent plant is 30 cm in height, while the claimed plant is 40 cm in height.

The objective of the hybridization of this rose variety for commercial culture was to create a new and distinct variety with unique qualities, such as:

1. Uniform and abundant pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpal055' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpal055' was selected by the inventor as a single plant from the progeny of the hybridization in 2007.

Asexual reproduction of 'Poulpal055' by cuttings was first done by Mogens N. Olesen in the nursery in Fredensborg, Denmark in 2008. This initial and other subsequent propagations conducted in controlled environments have demonstrated that the characteristics of 'Poulpal055' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal055'.

Specifically illustrated in FIG. 1 are an open flower, flower petals, and flower parts.

Figure 1:
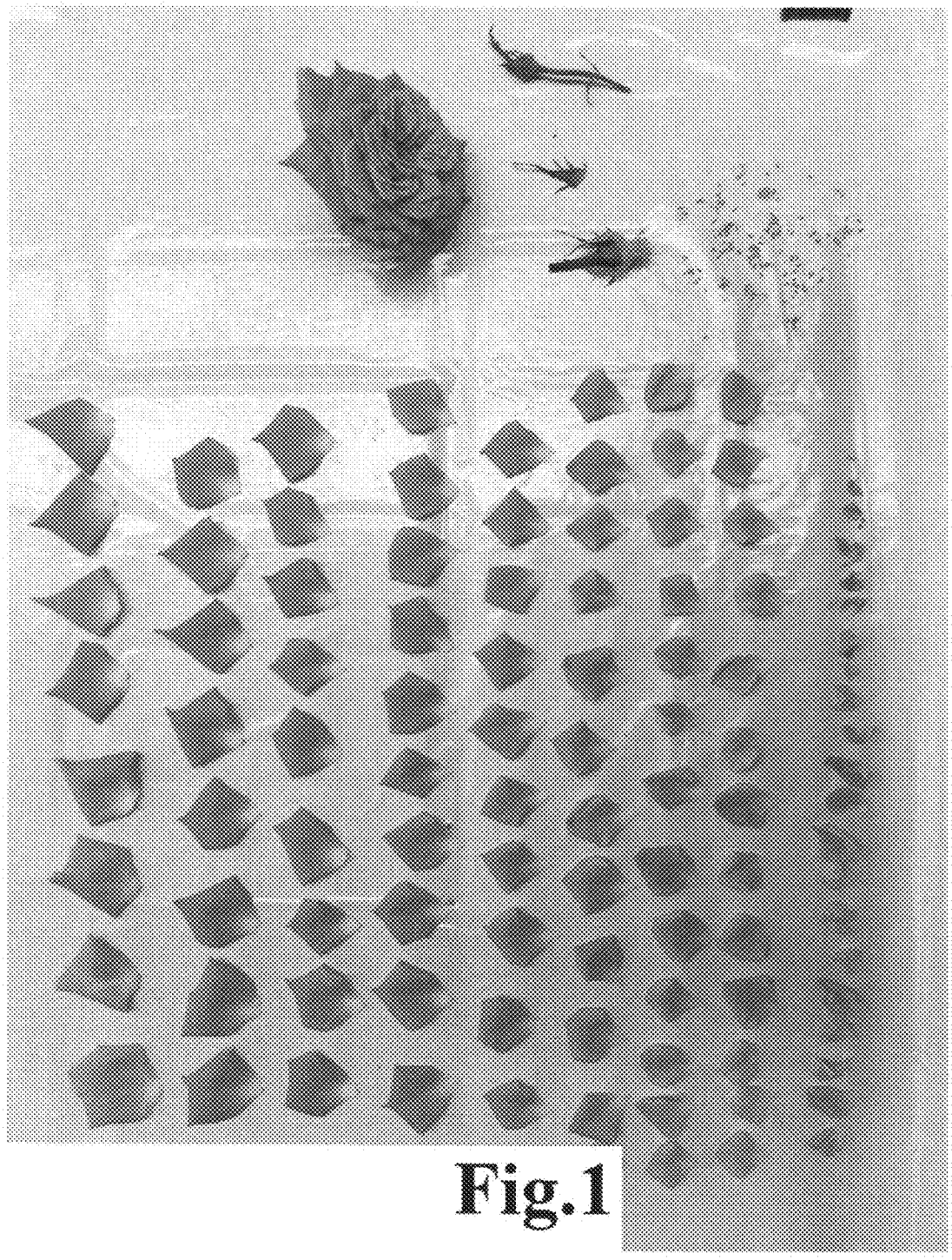
Figure 2:
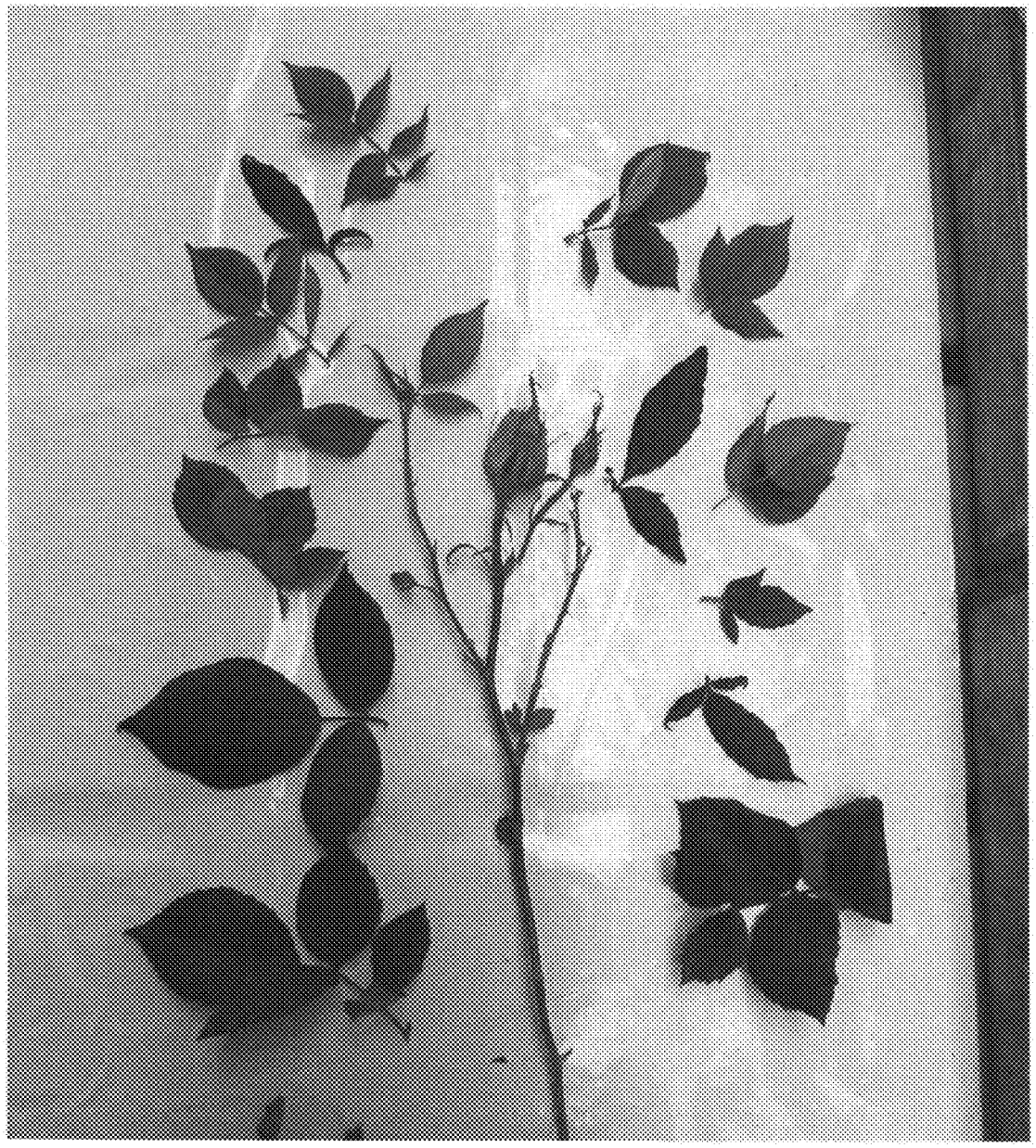

Specifically illustrated in FIG. 2 are flower bud, stems and leaves. Illustrated plants are 5 months of age.

DETAILED DESCRIPTION OF THE VARIETY

The following is a description of 'Poulpal055', as observed in its growth in a glasshouse in Denmark. Observed plants are 5 months of age, and were cultivated in 23 cm pots. Color references are made using The Royal Horticultural Society (London, England) Colour Chart, 2001, except where common terms of color are used.

For a comparison, several physical characteristics of the rose variety 'Poulpm002', U.S. Plant Pat. No. 15,383 are compared to 'Poulpal055' in Chart 1.

CHART 1

| | 'Poulpal055' | 'Poulpm002' |
|---|---|---|
| Petalage: | 100 petals total, 15 to 20 of which are petaloids | 26 to 30 petals |
| Flower Diameter: | 70 to 100 mm | 65 mm |
| General Tonality of Flower Color: | Red-Purple Group 68C | Red Group 55B to Red-Purple Group 63C |

FLOWER AND FLOWER BUD

Blooming habit: Continuous.

Flower bud:

*Size.*—Upon opening, 35 mm in length from base of receptacle to end of bud. 12 mm in diameter.

*Bud form.*—Urceolate.

*Bud color.*—As sepals unfold, petals are Red Group 39B.

*Sepals.*—Upper Surface: Color: Green Group 139C. Texture: Smooth, moderately pubescent. Lower Surface: Color: Yellow Green Group 144A. Texture: Smooth. Shape: Apex: Cirrhose. Base: Flat at union with receptacle. Margins: Margins have weak foliaceous appendages on three of the five sepals. Size: 40 mm long by 10 mm wide.

*Receptacle.*—Surface Texture: Smooth. Shape: Funnel shaped. Size: 5 mm tall and 10 mm wide. Color: Yellow Green Group 144A.

*Pedicel.*—Surface: Smooth with fine stipitate glands. Length: 35 mm on average. Diameter: Generally 3 mm. Color: Yellow-Green Group 144D. Strength: Medium strength.

*Borne.*—Singly or in clusters of 3.

*Peduncle.*—Surface: Smooth. Length: 8 to 12 cm. Diameter: 2 to 3 mm. Color: Yellow-Green Group 144A.

Flower bloom:

*Fragrance.*—Light floral scent.

*Duration.*—Flowers last up to 20 days.

*Size.*—Flower diameter is 70 to 100 mm when open. Flower depth is 30 to 40 mm.

*Form.*—General shape is a rosette with many slightly overlapping petals.

*Shape of flower, side view.*—The upper portion is a flattened convex. The lower portion is concave.

Petalage: Under normal conditions, flowers have 100 petals total, 15 to 20 of which are petaloids.

Color:

*General tonality.*—On open flower Red-Purple Group 68C.

*Upon opening, petals.*—Outermost and innermost petals are Red Group 39A on the upper surface. Red Group 39B on the lower surface. At the base of the petal, the upper surface is Yellow Group 7B and the lower surface is Yellow Group 10B.

*After opening, petals.*—Outermost petals are Red-Purple Group 68B on the upper surface. Red-Purple Group 68A on the lower surface. Innermost petals are Red-Purple Group 63C on the upper surface. Red-Purple Group 68B on the lower surface. At the base of the petal, the upper and lower surface is Yellow Group 8D.

Petals:

*Petal reflex.*—Outer petals reflex is strong.

*Margin.*—Entire, with weak undulations.

*Shape.*—Generally broad elliptic. Apex shape: Rounded, occasionally emarginate. Base shape: Acute and rounded.

*Size.*—40 to 50 mm (l) by 30 to 35 mm (w).

*Texture.*—Slightly textured.

*Thickness.*—Thin.

Petaloids:

*Quantity.*—15 to 20.

*Shape.*—Irregular, and asymmetric. The apex and base are acute.

*Color.*—Red-Purple Group 63C on the upper surface. Red-Purple Group 68B on the lower surface. At the base of the petaloid, the upper and lower surface are Yellow Group 8D.

*Size.*—10 to 30 mm (l) by 10 to 20 mm (w).

Reproductive organs:

*Pollen.*—None Observed.

*Anthers.*—Size: 2 mm long. Color: Greyed-Orange Group 167A. Quantity: 100 on average.

*Filaments.*—Color: Yellow Group 5A. Length: About 5 mm.

*Pistils.*—Length: About 10 mm long. Quantity: 100 on average.

*Stigmas.*—Color: Yellow-Orange Group 14A.

*Styles.*—Color: Yellow-Green Group 150C.

*Seed formation.*—Not observed.

PLANT

Plant growth: Upright to bushy. Plants are about 40 cm in height, and 40 cm wide.

Stems:

*Color.*—Juvenile growth: Yellow-Green Group 144A. Mature growth: Yellow-Green Group 146B.

*Length.*—Canes are 30 cm from the base of the plant to the flowering portion.

*Diameter.*—3 to 4 mm.

*Internodes.*—On mature canes, there is an average distance of 30 mm between nodes.

*Surface texture.*—Young and mature wood is smooth.

Prickles: None observed.

Plant foliage:

*Compound leaf size:* 70 to 130 mm (l) by 60 to 120 mm (w).

*Quantity:* 3 leaves per 10 cm of stem.

*Color of juvenile foliage.*—Upper Leaf Surface: Yellow-Green Group 146B. Lower Leaf Surface: Yellow-Green Group 147C.

*Color of mature foliage.*—Upper Leaf Surface: Green Group 139A. Lower Leaf Surface: Green Group 138A.

Plant leaves and leaflets:

*Stipules.*—Size: About 5 mm in length. Shape: Linear, slightly broad based with outward extending apecies. Margins: Finely serrated with few stipitate glands. Color: Yellow-Green Group 145A.

*Petiole*.—Length: 5 to 15 mm. Diameter: 1 to 2 mm. Upper surface: Yellow-Green Group 146A with stipitate glands. Lower surface: Yellow-Green Group 146C.

*Rachis*.—Length: 20 mm on average. Diameter: About 2 mm. Upper surface: Yellow-Green Group 147A with Greyed-Red Group anthocyanin. Lower surface: Yellow-Green Group 146C.

*Leaflet*.—Number of leaflets: 5 to 7 on normal leaves in middle of the stem. Size: 65 mm in length by 35 mm wide. Margin: Doubly serrate. General Shape: Ovate. Apex Shape: Mucronate. Base Shape: Round. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpal055', substantially as illustrated and described herein, due to its abundant, pink flowers, vigorous growth, compact habit, suitability for production from softwood cuttings in pots, and durable flowers and foliage that make the variety suitable for distribution in the floral industry.

* * * * *